(12) United States Patent
Perry

(10) Patent No.: US 6,246,966 B1
(45) Date of Patent: Jun. 12, 2001

(54) METHOD AND APPARATUS FOR DATA MANAGEMENT AUTHENTICATION IN A CLINICAL ANALYZER

(75) Inventor: Joseph E. Perry, Osceola, IN (US)

(73) Assignee: Bayer Corporation, Elkhart, IN (US)

( * ) Notice: Subject to any disclaimer, the term of this patent is extended or adjusted under 35 U.S.C. 154(b) by 0 days.

(21) Appl. No.: 09/055,385

(22) Filed: Apr. 6, 1998

(51) Int. Cl.[7] .................................................. G01D 18/00
(52) U.S. Cl. ............................................ 702/91; 600/368
(58) Field of Search ............................ 702/91, 62, 178, 702/187, 104, 116; 713/178, 184, 202; 600/319, 316, 322, 347, 365

(56) References Cited

U.S. PATENT DOCUMENTS

| 4,779,199 | * | 10/1988 | Yoneda et al. | 364/413.03 |
| 4,858,615 | * | 8/1989 | Meinema | 128/668 |
| 5,249,863 | * | 10/1993 | Brown | 374/102 |
| 5,715,390 | * | 2/1998 | Hoffman et al. | 395/188.01 |
| 5,839,094 | * | 11/1998 | French | 702/91 |
| 5,946,641 | * | 8/1999 | Morys | 702/91 |
| 5,987,155 | * | 11/1999 | Dunn et al. | 382/166 |

* cited by examiner

Primary Examiner—Kamini Shah
Assistant Examiner—Edward Raymond
(74) Attorney, Agent, or Firm—Jerome L. Jeffers

(57) ABSTRACT

A method and apparatus are provided for data management authentication in a clinical analyzer. The clinical analyzer includes a sensor for receiving a user sample to be measured and a processor for performing a predefined test sequence for measuring a predefined parameter value. A memory is coupled to the processor for storing predefined parameter data values. An authentication password is associated with each data transmission by the clinical analyzer and read by an associated computer system to validate each data transmission. The authentication password is generated by the clinical analyzer utilizing predetermined information in each data transfer.

9 Claims, 4 Drawing Sheets

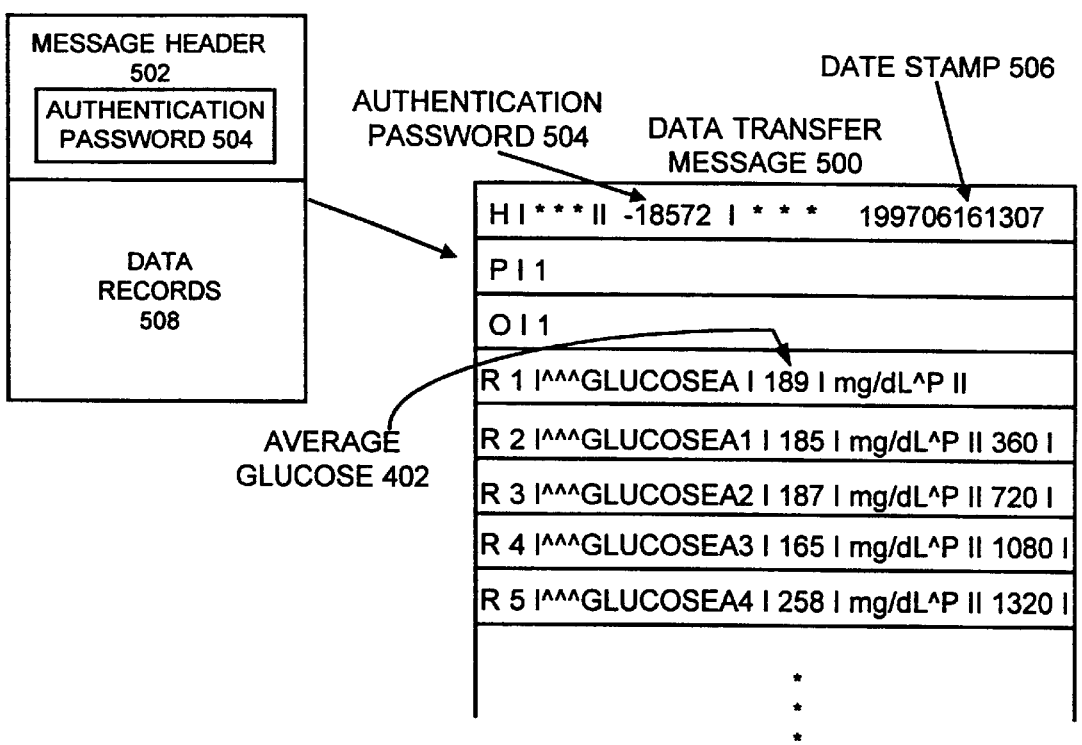

METHOD AND APPARATUS FOR DATA MANAGEMENT AUTHENTICATION IN A CLINICAL ANALYZER

FIELD OF THE INVENTION

The present invention generally relates to a clinical analyzer, and, more particularly, to a new and improved method and apparatus for data management authentication in a clinical analyzer.

DESCRIPTION OF THE PRIOR ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the procedure and apparatus of this invention can be used with other diagnostic systems.

Diagnostic systems, such as, blood glucose systems include a biosensor used to calculate the actual glucose value based on a measured output (either current or color) and the known reactivity of the reagent sensing element used to perform the test. The test results typically are displayed to the user and stored in a memory in the blood glucose monitor. It is desirable to periodically transfer the multiple stored values from the blood glucose monitor to a separate computer, for example to enable analysis by a doctor for the blood glucose monitor user.

One known communications protocol for such data transfer is the ASTM Standard E1381-91, "Specification for Low-Level Protocol to Transfer Messages Between Clinical Laboratory Meters and Computer Systems" and ASTM Standard E1394-91, "Standard Specifications for Transferring Information Between Clinical Meters and Computer Systems". ASTM Standard E1381-91 defines the low-level data transfer protocol and ASTM Standard E1394-91 defines the data format.

Multiple commercially available clinical analyzer are available for patient use. Due to differences between various commercially available clinical analyzer, a need exists for a method and apparatus for data management authentication in a clinical analyzer to validate data transmissions and to identify a particular type of clinical analyzer. Otherwise if a patient changes to a different type of clinical analyzer, then analysis by the patient's doctor of the data transfers from the different clinical analyzer likely would provide erroneous results.

SUMMARY OF THE INVENTION

Important objects of the present invention are to provide a new and improved method and apparatus for data management authentication in a clinical analyzer; to provide such method and apparatus that eliminates or minimizes the need for user interaction; and to provide such method and apparatus that overcome some disadvantages of prior art arrangements.

In brief, a method and apparatus are provided for data management authentication in a clinical analyzer. The clinical analyzer includes a sensor for receiving a user sample to be measured and a processor for performing a predefined test sequence for measuring a predefined parameter value. A memory is coupled to the processor for storing predefined parameter data values. An authentication password is associated with each data transmission by the clinical analyzer to an associated computer system. The authentication password is read by the associated computer system to validate each data transmission. The authentication password is generated by the clinical analyzer utilizing predetermined information in each data transmission.

BRIEF DESCRIPTION OF THE DRAWINGS

The present invention together with the above and other objects and advantages may best be understood from the following detailed description of the preferred embodiments of the invention illustrated in the drawings, wherein:

FIG. 5 is a chart illustrating an exemplary message format including an authentication password in accordance with the present invention of the clinical analyzer of FIG. 1.

DETAILED DESCRIPTION OF THE PREFERRED EMBODIMENTS

Figure 1:
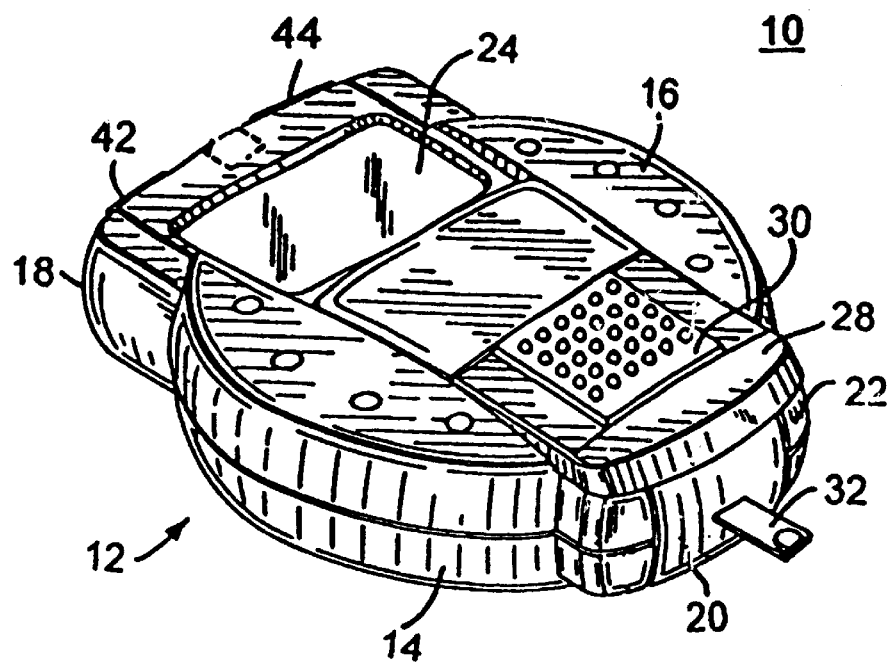
FIG. 1 is an enlarged perspective view of a clinical analyzer shown in an open position in accordance with the present invention.
Figure 2:
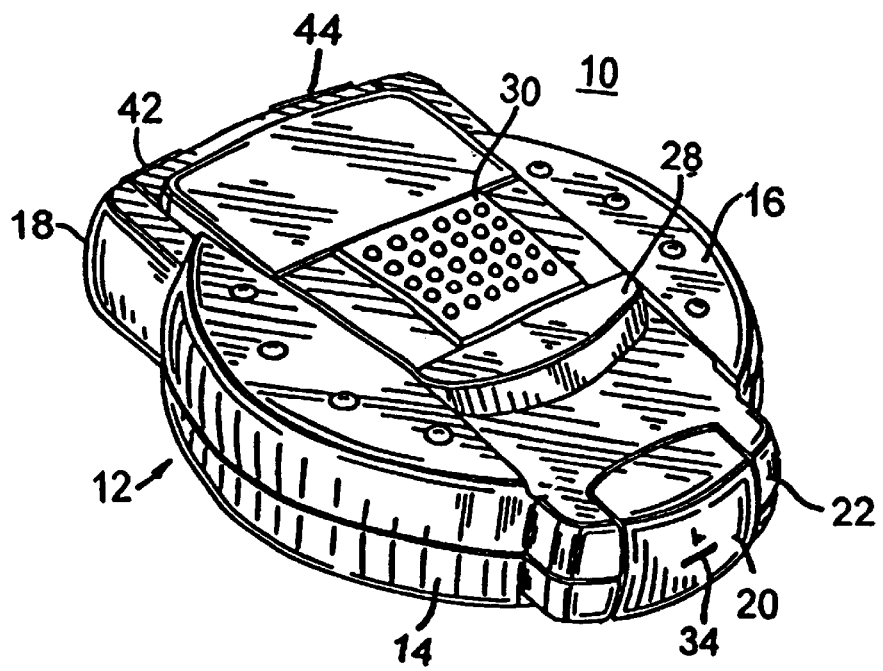
FIG. 2 is an enlarged perspective view of the clinical analyzer of FIG. 1 shown in a closed position.

Having reference now to the drawings, in FIGS. 1 and 2 there is illustrated a clinical analyzer designated as a whole by the reference character 10 and arranged in accordance with principles of the present invention. Clinical analyzer 10 includes a clam-shell type enclosure 12 formed by a base member 14 and a cover member 16. Base and cover members 14 and 16 are pivotably attached together at a first end 18 and are secured together by a latch member 20 at a second, opposite end 22. A display 24, such as a liquid crystal display (LCD) is carried by the cover member 16. To turn the clinical analyzer 10 on and off, a manually movable slide 28 mounted on the cover member 16 is moved between an open position shown in FIG. 1 and a closed position shown in FIG. 2.

In the closed or OFF position of FIG. 2. the slide 28 covers the display 24. A thumb grip 30 carried by the slide 28 is arranged for manual engagement by a user of the clinical analyzer 10 to select the ON and OFF positions. The thumb grip 30 also is movable from left to right in the OFF position of slide 28 for selecting a system test operational mode. When a user moves the slide 28 to the ON position of FIG. 1, the display is uncovered and a sensor 32 is presented. The sensor 32 extends through a slot 34 and is positioned outside the enclosure 12 for the user to apply a blood drop. A right button 42 and a left button or switch 44 (or switches A and B) are carried by the enclosure 12 for operation by a user to select predefined operational modes for the clinical analyzer 10, and for example, to set, recall and delete blood glucose readings and to set date, time, and options.

Figure 3:
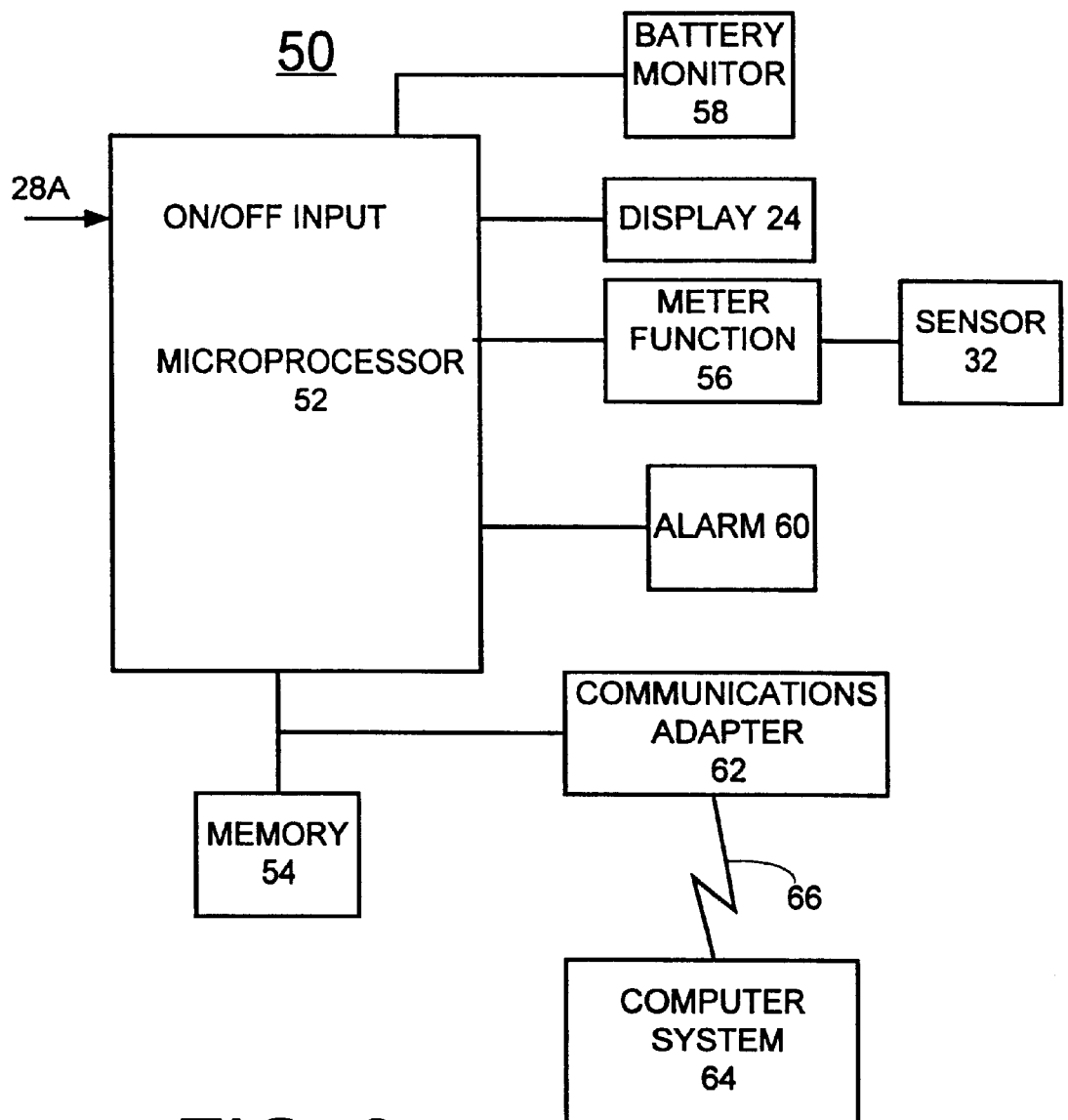
FIG. 3 is a block diagram representation of clinical analyzer circuitry in accordance with the present invention of the clinical analyzer of FIG. 1.

Referring also to FIG. 3, there is shown a block diagram representation of clinical analyzer circuitry designated as a whole by the reference character 50 and arranged in accordance with principles of the present invention. Clinical analyzer circuitry 50 includes a microprocessor 52 together with an associated memory 54 for storing program and user data. The display 24 is operatively controlled by the microprocessor 52. A meter function 56 coupled to the sensor 32 is operatively controlled by the microprocessor 52 for recording blood glucose test values. A battery monitor function 58 is coupled to the microprocessor 52 for detecting a dead battery (not shown) condition. An alarm function 60 is coupled to the microprocessor 52 for detecting predefined system conditions and for generating alarm indications for the user of clinical analyzer 10. A data port or communications adapter 62 couples data to and from a connected computer system 64 via a communications link 66. An ON/OFF input at a line 28A responsive to the user ON/OFF operation of the slide 28 is coupled to the microprocessor 52 for performing the blood test sequence mode of clinical analyzer 10. Microprocessor 52 contains suitable programming to perform the methods of the invention as illustrated in FIGS. 4 and 5.

In accordance with the invention, an authentication password generally designated by 504 in FIG. 5 is associated with each data transmission or message generally designated by 500 by the clinical analyzer 10. The authentication password 504 is read by the associated computer system 64 to validate each data transmission. The authentication password 504 is generated by the clinical analyzer 10 utilizing predetermined information in each data transmission.

Figure 4:
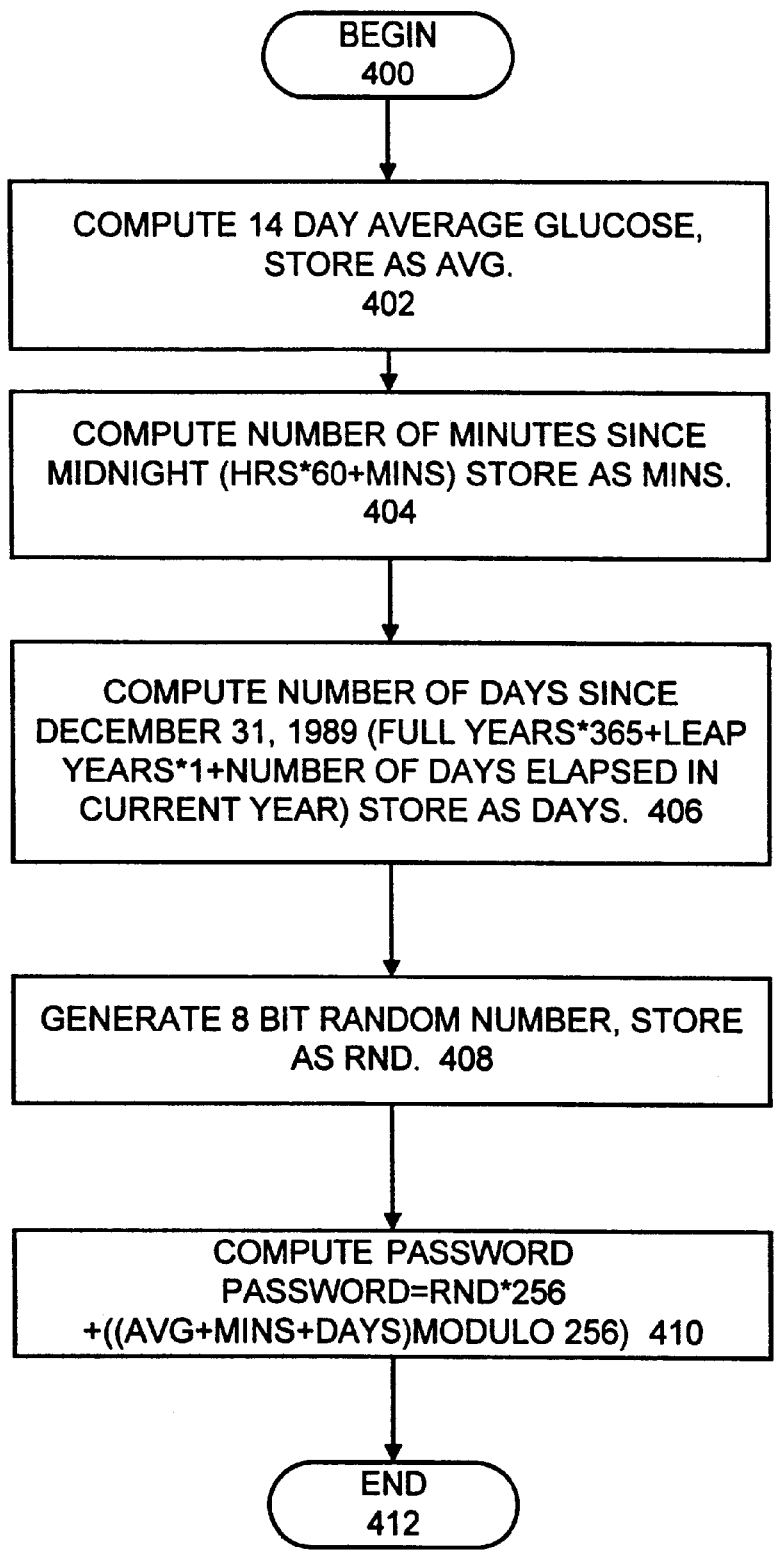
FIG. 4 is a flow chart illustrating exemplary sequential steps of a data management authentication method in accordance with the present invention of the clinical analyzer of FIG. 1.

Referring to FIG. 4, there are shown exemplary steps for password computation of the invention starting at a block 400. First a fourteen day average glucose is computed and stored as AVG as indicated at a block 402. A number of minutes since midnight (hrs*sixty+mins), is computed and stored as MINS as indicated at a block 404. A number of days since an predetermined date, such as Dec. 31, 1989, to the present date is computed, (full years*three hundred sixty five+leap years*one+number of days elapsed in current year), and stored as DAYS as indicated at a block 406. An eight bit random number is generated and stored as RND as indicated at a block 408. Then the password is computed, passwd=RND*two hundred fifty six+((AVG +MINS+ DAYS) MODULO two hundred fifty six) as indicated at a block 410. This completes the sequential steps as indicated at a block 412.

FIG. 5 illustrates an exemplary message format generally designated by 500 of the invention used for each data transfer from the clinical analyzer 10 to the associated computer system 64. Each data transfer or message 500 includes a message header 502 including a predefined field containing the authentication password 504. Another predefined field in the message header 502 contains a current date stamp 506 for the message 500. Each data transfer or message 500 includes a plurality of data records 508. In FIG. 5, five example data records 508 are shown and labeled R1, R2, R3, R4 and R5. An authentication password 504 of −18572 is shown with a date stamp 506 of Jun. 16, 1997, time 1307 or 1:07PM. The fourteen day average glucose is shown as 189 in record R1 including the universal test ID is "∧∧∧GlucoseA".

The ASTh E1394-91 standard defines a header record that advantageously is used for the message header 502. The authentication password 504 is contained in one field within the header record defined as an "access password" field by the ASTM E1394-91 standard. The clinical analyzer 10 transmits the authentication password 504 as a signed integer, a 16 bit value. The signed integer is actually transmitted as a sequence of ASCII (American National Standard for Information Interchange) characters which represent the integer. The range for the authentication password 504 is from "−32767" to "32768".

The eight most significant bits of the authentication password 504 is an 8-bit random number, that must change randomly from transmission to transmission of messages 500. The eight least significant bits of the authentication password 504 is based on the date and time of the message contained in time stamp field 506 of the header record 502 and the 14 day average glucose contained in a result record 508 when the universal test ID is "∧∧∧GlucoseA", as shown in data record RI in FIG. 5. The computed part of the password is calculated by adding the number of minutes since midnight to the number of days since Dec. 31, 1989, plus the 14 day average glucose (in mg/dL). Only the 8 least significant bits of the computation are kept. If the clinical analyzer 10 provides glucose values in mmol/L, then the 14 day average value is first converted to mg/dL (multiply by 18 and rounded to an integer) before being added in the password calculation.

The 8-bit random part (most significant byte) is concatenated to the 8-bit computed part (least significant byte) which results in a 16 bit value for the authentication password 504. The authentication password 504 is interpreted as a 16 bit signed integer ranging in value from −32767 to 32768. It is transmitted as the sequence of ASCII characters which represent the integer.

When computer system 64 receives the transmission from a particular clinical analyzer 10, it converts the ASCII characters in the password field to an integer. The 8 most significant bits are ignored, the 8 least significant bits are verified against the calculation of the authentication password 504 as detailed above. For example, the authentication password 504 of −18572 is compared with a computed value by the computer system 64. The computer system 64 uses the same equation, shown in block 410 in FIG. 4 for computing the authentication password 504, as used by the clinical analyzer 10. The DAYS value of the number of days since Dec. 31, 1989 until the date stamp date of Jun. 16, 1997 is calculated by (7 full years*three hundred sixty five+2 leap years*one day/leap-year+number of days elapsed in current year (31+28+31+30+31+16) which equals 2724. The time calculation (minutes since midnight) equals ((13 hours*60 minutes/hour)+7 minutes) which equals 787. The computation is verified as follows (2724+787+189) which equals 3700 or OE74 total in hexadecimal, keeping the least significant 8-bits in hexadecimal or 74 in hexadecimal which equals 116 decimal. The access password is −18572 in decimal or B774 in hexadecimal. Keeping the least significant bits of the result leave 74 in hexadecimal which equals 116 decimal. Thus, the authentication password 504 agrees with the computed value for the example data transfer message 500 of FIG. 5. Only when the authentication password 504 agrees with the computed value is the clinical analyzer 10 identified as a valid meter.

While the present invention has been described with reference to the details of the embodiments of the invention shown in the drawings, these details are not intended to limit the scope of the invention as claimed in the appended claims.

What is claimed is:

1. A clinical analyzer comprising:

sensor means for receiving a user sample;

processor means responsive to said sensor means for performing a predefined test sequence for measuring a predefined parameter value;

memory means coupled to said processor means for storing said predefined parameter data value;

communications means coupled to said processor means for transferring data to a computer system; each said data transfer including an authentication password and a plurality of said predefined parameter data values; said authentication password used by said computer system to validate each said data transfer and said authentication password being generated by said processor means utilizing predetermined information in each data transfer.

2. A clinical analyzer as recited in claim 1 wherein said predetermined information in each data transfer includes a time stamp value.

3. A clinical analyzer as recited in claim 2 wherein said time stamp value includes a current date and time value for said data transfer.

4. A clinical analyzer as recited in claim 3 wherein said predetermined information in each data transfer includes a fourteen day average glucose value.

5. A clinical analyzer as recited in claim 1 wherein each said data transfer includes said authentication password in a message header and said predefined parameter data values are included in a plurality of results records, said results records following said message header.

6. A clinical analyzer as recited in claim 5 wherein said message header includes a current time stamp value for said data transfer.

7. A clinical analyzer as recited in claim 6 wherein one of said plurality of results records includes a fourteen day average glucose value.

8. A clinical analyzer as recited in claim 7 wherein said wherein said authentication password generated by said processor means is read and compared with a calculated value by said computer system utilizing said current time stamp value and said fourteen day average glucose value.

9. A method for validating each data transfer from a clinical analyzer to a computer system comprising the steps of:

providing the clinical analyzer with a sensor for receiving a user sample and a processor for performing a predefined test sequence for measuring a predefined parameter value;

storing a plurality of said predefined parameter values, and transferring stored data to a computer system including said predefined parameter values and an authentication password; each said data transfer including the step of calculating said authentication password by said processor utilizing predetermined information in each said data transfer, and transferring said authentication password and said predefined parameter data values to said computer system; said authentication password used by said computer system to validate each said data transfer.

* * * * *